US011844812B2

(12) United States Patent
Bergmann et al.

(10) Patent No.: US 11,844,812 B2
(45) Date of Patent: Dec. 19, 2023

(54) SELENOPROTEIN P FOR PREDICTION OF A FIRST CARDIOVASCULAR EVENT

(71) Applicant: SPHINGOTEC GMBH, Hennigsdorf (DE)

(72) Inventors: Andreas Bergmann, Berlin (DE); Olle Melander, Limhamm (SE)

(73) Assignee: SPHINGOTEC GMBH, Hennigsdorf (DE)

(*) Notice: Subject to any disclaimer, the term of this patent is extended or adjusted under 35 U.S.C. 154(b) by 545 days.

(21) Appl. No.: 16/758,648

(22) PCT Filed: Oct. 23, 2018

(86) PCT No.: PCT/EP2018/079030
§ 371 (c)(1),
(2) Date: Apr. 23, 2020

(87) PCT Pub. No.: WO2019/081504
PCT Pub. Date: May 2, 2019

(65) Prior Publication Data
US 2020/0348315 A1 Nov. 5, 2020

(30) Foreign Application Priority Data

Oct. 24, 2017 (EP) .................................. 17198129
Mar. 16, 2018 (EP) .................................. 18162206

(51) Int. Cl.
*A61K 33/04* (2006.01)
*G16B 20/50* (2019.01)
*A61K 31/198* (2006.01)
*G01N 33/68* (2006.01)

(52) U.S. Cl.
CPC .......... *A61K 33/04* (2013.01); *A61K 31/198* (2013.01); *G01N 33/6893* (2013.01); *G16B 20/50* (2019.02); *G01N 2800/32* (2013.01); *G01N 2800/50* (2013.01)

(58) Field of Classification Search
CPC ...... A61K 33/04; A61K 31/198; G16B 20/50; G01N 33/6893; G01N 2800/32; G01N 2800/50
USPC ....................................................... 702/23
See application file for complete search history.

(56) References Cited

U.S. PATENT DOCUMENTS

| 2012/0003751 | A1 | 1/2012 | Bergmann et al. | |
| 2015/0118236 | A1 | 4/2015 | Bergmann et al. | |
| 2017/0089924 | A1* | 3/2017 | Shimokawa | ....... G01N 33/6893 |
| 2017/0102396 | A1 | 4/2017 | Hess et al. | |

FOREIGN PATENT DOCUMENTS

| CN | 101637301 A | 2/2010 |
| CN | 101953511 A | 1/2011 |
| JP | WO 2015/163098 | * 10/2015 |
| WO | 10040564 A1 | 4/2010 |
| WO | 13132088 A1 | 9/2013 |
| WO | 15185672 A2 | 12/2015 |

OTHER PUBLICATIONS

Hollenbach et al. New assay for the measurement of selenoprotein P as a sepsis biomarker from serum. Journal of Trace Elements in Medicine and Biology 22 (2008) 24-32. (Year: 2008).*
Andoh et al. Serum selenoprotein-P levels in patients with inflammatory bowel disease. Nutrition 21 (2005) 574-579. (Year: 2005).*
Koyama H et al: "Depressed serum selenoprotein P: possible new predicator of increased risk for cerebrovascular events", Nutrition Research, Elsevier Inc, XX, vol. 29, No. 2, Feb. 1, 2009 (Feb. 1, 2009), pp. 94-99, XP025973441, ISSN: 0271-5317.
Mojgan Gharipour et al: "Association of expression of selenoprotein P in mRNA and protein levels with metabolic syndrome in subjects with cardiovascular disease: Results of the Selenegene study", Journal of Gene Medicine, vol. 19, No. 3, Mar. 1, 2017 (Mar. 1, 2017), US, pp. e2945, XP055487167, ISSN: 1099-498X.
Gharipour Mojgan et al.: "Selenium Homeostasis and Clustering of Cardiovascular Risk Factors: A Systematic Review.", ACTA Bio-Medica : Atenei Parmensis Oct. 23, 2017, vol. 88, No. 3, Oct. 23, 2017 (Oct. 23, 2017), pp. 263-270, XP002782458, ISSN: 0392-4203.
Urban Alehagen et al: "Reduced Cardiovascular Mortality 10 Years after Supplementation with Selenium and Coenzyme Q10 for Four Years: Follow-Up Results of a Prospective Randomized Double-Blind Placebo-Controlled Trial in Elderly Citizens", PLOS One, vol. 10, No. 12, Dec. 1, 2015 (Dec. 1, 2015), pp. e0141641, XP055487164.
Saverio Stranges et al: "Effects of Selenium Supplementation on Cardiovascular Disease Incidence and Mortality: Secondary Analyses in a Randomized Clinical Trial", American Journal of Epidemiology, vol. 163, No. 8, Feb. 22, 2006 (Feb. 22, 2006), US, pp. 694-699, XP055547028, ISSN: 0002-9262.
Chortyk Orestes T et al: "Increasing selenium in cigarettes and smoke: transfer to smoke", Archives of Environmental HE, Washington DC, US, vol. 39, No. 6, Jan. 1, 1984 (Jan. 1, 1984), pp. 419-424, XP009190270, ISSN: 0003-9896.
Gemma Flores-Mateo et al: "Selenium and coronary heart disease: a meta-analysis", The American Journal of Clinical Nutrition, vol. 84, No. 4, Oct. 1, 2006 (Oct. 1, 2006), US, pp. 762-773, KP055546848, ISSN: 0002-9165.

(Continued)

*Primary Examiner* — Yih-Horng Shiao
(74) *Attorney, Agent, or Firm* — MILLEN, WHITE, ZELANO & BRANIGAN, PC; Ryan Pool

(57) ABSTRACT

Subject of the present invention is a method for assessing a risk for getting a first cardiovascular event or assessing the risk for cardiovascular mortality in a subject, comprising: a) determining the level and/or the amount of Selenoprotein P and/or fragments thereof in a sample of said subject; b) correlating the determined level and/or the amount of Selenoprotein P and/or fragments thereof with the risk for getting a first cardiovascular event or assessing the risk for cardiovascular mortality in said subject.

10 Claims, 2 Drawing Sheets

Figure 1:
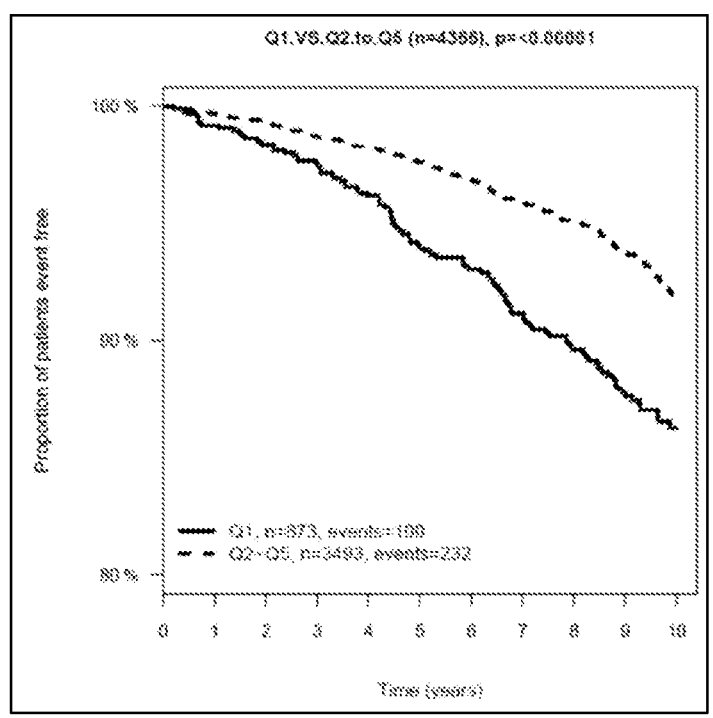

Specification includes a Sequence Listing.

(56) References Cited

OTHER PUBLICATIONS

Alehagen Urban et al: "Cardiovascular mortality and N-terminal-proBNP reduced after combined selenium and coenzyme Q10 supplementation: A 5-year prospective randomized double-blind placebo-controlled trial among elderly Swedish citizens", International Journal of Cardiology, vol. 167, No. 5, May 23, 2012 (May 23, 2012), pp. 1860-1866, XP028703319, ISSN: 0167-5273.
International Search Report PCT/ EP2018/079030 dated Feb. 15, 2019 pp. 1-9.

* cited by examiner

SEQUENCE LISTING

<160> NUMBER OF SEQ ID NOS: 15

<210> SEQ ID NO 1
<211> LENGTH: 381
<212> TYPE: PRT
<213> ORGANISM: Homo sapiens
<220> FEATURE:
<221> NAME/KEY: UNSURE
<222> LOCATION: (1)..(381)
<223> OTHER INFORMATION: Xaa or single letter X represents
      Selenocystein (U) in originally disclosed sequence

<400> SEQUENCE: 1

Met Trp Arg Ser Leu Gly Leu Ala Leu Ala Leu Cys Leu Leu Pro Ser
1               5                   10                  15

Gly Gly Thr Glu Ser Gln Asp Gln Ser Ser Leu Cys Lys Gln Pro Pro
            20                  25                  30

Ala Trp Ser Ile Arg Asp Gln Asp Pro Met Leu Asn Ser Asn Gly Ser
        35                  40                  45

Val Thr Val Val Ala Leu Leu Gln Ala Ser Xaa Tyr Leu Cys Ile Leu
    50                  55                  60

Gln Ala Ser Lys Leu Glu Asp Leu Arg Val Lys Leu Lys Lys Glu Gly
65                  70                  75                  80

Tyr Ser Asn Ile Ser Tyr Ile Val Val Asn His Gln Gly Ile Ser Ser
                85                  90                  95

```
Arg Leu Lys Tyr Thr His Leu Lys Asn Lys Val Ser Glu His Ile Pro
                100                 105                 110

Val Tyr Gln Gln Glu Glu Asn Gln Thr Asp Val Trp Thr Leu Leu Asn
            115                 120                 125

Gly Ser Lys Asp Asp Phe Leu Ile Tyr Asp Arg Cys Gly Arg Leu Val
        130                 135                 140

Tyr His Leu Gly Leu Pro Phe Ser Phe Leu Thr Phe Pro Tyr Val Glu
145                 150                 155                 160

Glu Ala Ile Lys Ile Ala Tyr Cys Glu Lys Cys Gly Asn Cys Ser
                165                 170                 175

Leu Thr Thr Leu Lys Asp Glu Asp Phe Cys Lys Arg Val Ser Leu Ala
                180                 185                 190

Thr Val Asp Lys Thr Val Glu Thr Pro Ser Pro His Tyr His His Glu
            195                 200                 205

His His His Asn His Gly His Gln His Leu Gly Ser Ser Glu Leu Ser
        210                 215                 220

Glu Asn Gln Gln Pro Gly Ala Pro Asn Ala Pro Thr His Pro Ala Pro
225                 230                 235                 240

Pro Gly Leu His His His His Lys His Lys Gly Gln His Arg Gln Gly
                245                 250                 255

His Pro Glu Asn Arg Asp Met Pro Ala Ser Glu Asp Leu Gln Asp Leu
            260                 265                 270

Gln Lys Lys Leu Cys Arg Lys Arg Cys Ile Asn Gln Leu Leu Cys Lys
        275                 280                 285

Leu Pro Thr Asp Ser Glu Leu Ala Pro Arg Ser Xaa Cys Cys His Cys
290                 295                 300

Arg His Leu Ile Phe Glu Lys Thr Gly Ser Ala Ile Thr Xaa Gln Cys
305                 310                 315                 320

Lys Glu Asn Leu Pro Ser Leu Cys Ser Xaa Gln Gly Leu Arg Ala Glu
                325                 330                 335

Glu Asn Ile Thr Glu Ser Cys Gln Xaa Arg Leu Pro Pro Ala Ala Xaa
            340                 345                 350

Gln Ile Ser Gln Gln Leu Ile Pro Thr Glu Ala Ser Ala Ser Xaa Arg
        355                 360                 365

Xaa Lys Asn Gln Ala Lys Lys Xaa Glu Xaa Pro Ser Asn
370                 375                 380

<210> SEQ ID NO 2
<211> LENGTH: 362
<212> TYPE: PRT
<213> ORGANISM: Homo sapiens
<220> FEATURE:
<221> NAME/KEY: UNSURE
<222> LOCATION: (1)..(362)
<223> OTHER INFORMATION: Xaa or single letter X represents
      Selenocystein (U) in originally disclosed sequence

<400> SEQUENCE: 2

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
        35                  40                  45

Lys Leu Glu Asp Leu Arg Val Lys Leu Lys Lys Glu Gly Tyr Ser Asn
    50                  55                  60
```

```
Ile Ser Tyr Ile Val Val Asn His Gln Gly Ile Ser Arg Leu Lys
 65                  70                  75                  80

Tyr Thr His Leu Lys Asn Lys Val Ser Glu His Ile Pro Val Tyr Gln
                 85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125

Gly Leu Pro Phe Ser Phe Leu Thr Phe Pro Tyr Val Glu Glu Ala Ile
    130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg Ser Xaa Cys Cys His Cys Arg His Leu
        275                 280                 285

Ile Phe Glu Lys Thr Gly Ser Ala Ile Thr Xaa Gln Cys Lys Glu Asn
    290                 295                 300

Leu Pro Ser Leu Cys Ser Xaa Gln Gly Leu Arg Ala Glu Glu Asn Ile
305                 310                 315                 320

Thr Glu Ser Cys Gln Xaa Arg Leu Pro Pro Ala Ala Xaa Gln Ile Ser
                325                 330                 335

Gln Gln Leu Ile Pro Thr Glu Ala Ser Ala Ser Xaa Arg Xaa Lys Asn
            340                 345                 350

Gln Ala Lys Lys Xaa Glu Xaa Pro Ser Asn
        355                 360
```

<210> SEQ ID NO 3
<211> LENGTH: 327
<212> TYPE: PRT
<213> ORGANISM: Homo sapiens
<220> FEATURE:
<221> NAME/KEY: UNSURE
<222> LOCATION: (1)..(327)
<223> OTHER INFORMATION: Xaa or single letter X represents
    Selenocystein (U) in originally disclosed sequence

<400> SEQUENCE: 3

```
Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
        35                  40                  45
```

```
Lys Leu Glu Asp Leu Arg Val Lys Leu Lys Lys Glu Gly Tyr Ser Asn
 50                  55                  60

Ile Ser Tyr Ile Val Val Asn His Gln Gly Ile Ser Ser Arg Leu Lys
 65                  70                  75                  80

Tyr Thr His Leu Lys Asn Lys Val Ser Glu His Ile Pro Val Tyr Gln
                 85                  90                  95

Gln Glu Glu Asn Gln Thr Asp Val Trp Thr Leu Leu Asn Gly Ser Lys
                100                 105                 110

Asp Asp Phe Leu Ile Tyr Asp Arg Cys Gly Arg Leu Val Tyr His Leu
                115                 120                 125

Gly Leu Pro Phe Ser Phe Leu Thr Phe Pro Tyr Val Glu Ala Ile
130                 135                 140

Lys Ile Ala Tyr Cys Glu Lys Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His Glu His His His
                180                 185                 190

Asn His Gly His Gln His Leu Gly Ser Ser Glu Leu Ser Glu Asn Gln
                195                 200                 205

Gln Pro Gly Ala Pro Asn Ala Pro Thr His Pro Ala Pro Pro Gly Leu
                210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
                260                 265                 270

Asp Ser Glu Leu Ala Pro Arg Ser Xaa Cys Cys His Cys Arg His Leu
                275                 280                 285

Ile Phe Glu Lys Thr Gly Ser Ala Ile Thr Xaa Gln Cys Lys Glu Asn
                290                 295                 300

Leu Pro Ser Leu Cys Ser Xaa Gln Gly Leu Arg Ala Glu Glu Asn Ile
305                 310                 315                 320

Thr Glu Ser Cys Gln Xaa Arg
                325

<210> SEQ ID NO 4
<211> LENGTH: 279
<212> TYPE: PRT
<213> ORGANISM: Homo sapiens
<220> FEATURE:
<221> NAME/KEY: UNSURE
<222> LOCATION: (1)..(279)
<223> OTHER INFORMATION: Xaa or single letter X represents
      Selenocystein (U) in originally disclosed sequence

<400> SEQUENCE: 4

Glu Ser Gln Asp Gln Ser Ser Leu Cys Lys Gln Pro Pro Ala Trp Ser
 1                   5                  10                  15

Ile Arg Asp Gln Asp Pro Met Leu Asn Ser Asn Gly Ser Val Thr Val
                 20                  25                  30

Val Ala Leu Leu Gln Ala Ser Xaa Tyr Leu Cys Ile Leu Gln Ala Ser
             35                  40                  45

Lys Leu Glu Asp Leu Arg Val Lys Leu Lys Lys Glu Gly Tyr Ser Asn
 50                  55                  60
```

```
Ile Ser Tyr Ile Val Val Asn His Gln Gly Ile Ser Ser Arg Leu Lys
 65                  70                  75                  80

Tyr Thr His Leu Lys Asn Lys Val Ser Glu His Ile Pro Val Tyr Gln
                 85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125

Gly Leu Pro Phe Ser Phe Leu Thr Phe Pro Tyr Val Glu Glu Ala Ile
    130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg
        275

<210> SEQ ID NO 5
<211> LENGTH: 280
<212> TYPE: PRT
<213> ORGANISM: Homo sapiens
<220> FEATURE:
<221> NAME/KEY: UNSURE
<222> LOCATION: (1)..(280)
<223> OTHER INFORMATION: Xaa or single letter X represents
      Selenocystein (U) in originally disclosed sequence

<400> SEQUENCE: 5

Glu Ser Gln Asp Gln Ser Ser Leu Cys Lys Gln Pro Pro Ala Trp Ser
1               5                  10                  15

Ile Arg Asp Gln Asp Pro Met Leu Asn Ser Asn Gly Ser Val Thr Val
                20                  25                  30

Val Ala Leu Leu Gln Ala Ser Xaa Tyr Leu Cys Ile Leu Gln Ala Ser
            35                  40                  45

Lys Leu Glu Asp Leu Arg Val Lys Leu Lys Lys Glu Gly Tyr Ser Asn
        50                  55                  60

Ile Ser Tyr Ile Val Val Asn His Gln Gly Ile Ser Ser Arg Leu Lys
 65                  70                  75                  80

Tyr Thr His Leu Lys Asn Lys Val Ser Glu His Ile Pro Val Tyr Gln
                 85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125
```

```
Gly Leu Pro Phe Ser Phe Leu Thr Phe Pro Tyr Val Glu Glu Ala Ile
            130                 135                 140
Lys Ile Ala Tyr Cys Glu Lys Cys Gly Asn Cys Ser Leu Thr Thr
145                 150                 155                 160
Leu Lys Asp Glu Asp Phe Cys Lys Arg Val Ser Leu Ala Thr Val Asp
                165                 170                 175
Lys Thr Val Glu Thr Pro Ser Pro His Tyr His His Glu His His His
                180                 185                 190
Asn His Gly His Gln His Leu Gly Ser Ser Glu Leu Ser Glu Asn Gln
                195                 200                 205
Gln Pro Gly Ala Pro Asn Ala Pro Thr His Pro Ala Pro Pro Gly Leu
            210                 215                 220
His His His His Lys His Lys Gly Gln His Arg Gln Gly His Pro Glu
225                 230                 235                 240
Asn Arg Asp Met Pro Ala Ser Glu Asp Leu Gln Asp Leu Gln Lys Lys
                245                 250                 255
Leu Cys Arg Lys Arg Cys Ile Asn Gln Leu Leu Cys Lys Leu Pro Thr
                260                 265                 270
Asp Ser Glu Leu Ala Pro Arg Ser
            275                 280

<210> SEQ ID NO 6
<211> LENGTH: 281
<212> TYPE: PRT
<213> ORGANISM: Homo sapiens
<220> FEATURE:
<221> NAME/KEY: UNSURE
<222> LOCATION: (1)..(281)
<223> OTHER INFORMATION: Xaa or single letter X represents
      Selenocystein (U) in originally disclosed sequence

<400> SEQUENCE: 6

Glu Ser Gln Asp Gln Ser Ser Leu Cys Lys Gln Pro Pro Ala Trp Ser
1               5                   10                  15
Ile Arg Asp Gln Asp Pro Met Leu Asn Ser Asn Gly Ser Val Thr Val
                20                  25                  30
Val Ala Leu Leu Gln Ala Ser Xaa Tyr Leu Cys Ile Leu Gln Ala Ser
            35                  40                  45
Lys Leu Glu Asp Leu Arg Val Lys Leu Lys Lys Glu Gly Tyr Ser Asn
50                  55                  60
Ile Ser Tyr Ile Val Val Asn His Gln Gly Ile Ser Ser Arg Leu Lys
65                  70                  75                  80
Tyr Thr His Leu Lys Asn Lys Val Ser Glu His Ile Pro Val Tyr Gln
                85                  90                  95
Gln Glu Glu Asn Gln Thr Asp Val Trp Thr Leu Leu Asn Gly Ser Lys
            100                 105                 110
Asp Asp Phe Leu Ile Tyr Asp Arg Cys Gly Arg Leu Val Tyr His Leu
        115                 120                 125
Gly Leu Pro Phe Ser Phe Leu Thr Phe Pro Tyr Val Glu Glu Ala Ile
            130                 135                 140
Lys Ile Ala Tyr Cys Glu Lys Cys Gly Asn Cys Ser Leu Thr Thr
145                 150                 155                 160
Leu Lys Asp Glu Asp Phe Cys Lys Arg Val Ser Leu Ala Thr Val Asp
                165                 170                 175
Lys Thr Val Glu Thr Pro Ser Pro His Tyr His His Glu His His His
                180                 185                 190
```

-continued

```
Asn His Gly His Gln His Leu Gly Ser Ser Glu Leu Ser Glu Asn Gln
            195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
                260                 265                 270

Asp Ser Glu Leu Ala Pro Arg Ser Xaa
            275                 280

<210> SEQ ID NO 7
<211> LENGTH: 282
<212> TYPE: PRT
<213> ORGANISM: Homo sapiens
<220> FEATURE:
<221> NAME/KEY: UNSURE
<222> LOCATION: (1)..(282)
<223> OTHER INFORMATION: Xaa or single letter X represents
      Selenocystein (U) in originally disclosed sequence

<400> SEQUENCE: 7

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
        35                  40                  45

Lys Leu Glu Asp Leu Arg Val Lys Leu Lys Lys Glu Gly Tyr Ser Asn
    50                  55                  60

Ile Ser Tyr Ile Val Val Asn His Gln Gly Ile Ser Ser Arg Leu Lys
65                  70                  75                  80

Tyr Thr His Leu Lys Asn Lys Val Ser Glu His Ile Pro Val Tyr Gln
                85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125

Gly Leu Pro Phe Ser Phe Leu Thr Phe Pro Tyr Val Glu Glu Ala Ile
    130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255
```

Leu Cys Arg Lys Arg Cys Ile Asn Gln Leu Leu Cys Lys Leu Pro Thr
        260                 265                 270

Asp Ser Glu Leu Ala Pro Arg Ser Xaa Cys
        275                 280

<210> SEQ ID NO 8
<211> LENGTH: 283
<212> TYPE: PRT
<213> ORGANISM: Homo sapiens
<220> FEATURE:
<221> NAME/KEY: UNSURE
<222> LOCATION: (1)..(283)
<223> OTHER INFORMATION: Xaa or single letter X represents
      Selenocystein (U) in originally disclosed sequence

<400> SEQUENCE: 8

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
        35                  40                  45

Lys Leu Glu Asp Leu Arg Val Lys Leu Lys Glu Gly Tyr Ser Asn
50                  55                  60

Ile Ser Tyr Ile Val Val Asn His Gln Gly Ile Ser Ser Arg Leu Lys
65                  70                  75                  80

Tyr Thr His Leu Lys Asn Lys Val Ser Glu His Ile Pro Val Tyr Gln
                85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125

Gly Leu Pro Phe Ser Phe Leu Thr Phe Pro Tyr Val Glu Glu Ala Ile
    130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg Ser Xaa Cys Cys
        275                 280

<210> SEQ ID NO 9
<211> LENGTH: 284
<212> TYPE: PRT
<213> ORGANISM: Homo sapiens
<220> FEATURE:

<221> NAME/KEY: UNSURE
<222> LOCATION: (1)..(284)
<223> OTHER INFORMATION: Xaa or single letter X represents
      Selenocystein (U) in originally disclosed sequence

<400> SEQUENCE: 9

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
        35                  40                  45

Lys Leu Glu Asp Leu Arg Val Lys Leu Lys Lys Glu Gly Tyr Ser Asn
50                  55                  60

Ile Ser Tyr Ile Val Val Asn His Gln Gly Ile Ser Ser Arg Leu Lys
65                  70                  75                  80

Tyr Thr His Leu Lys Asn Lys Val Ser Glu His Ile Pro Val Tyr Gln
                85                  90                  95

Gln Glu Glu Asn Gln Thr Asp Val Trp Thr Leu Leu Asn Gly Ser Lys
            100                 105                 110

Asp Asp Phe Leu Ile Tyr Asp Arg Cys Gly Arg Leu Val Tyr His Leu
        115                 120                 125

Gly Leu Pro Phe Ser Phe Leu Thr Phe Pro Tyr Val Glu Glu Ala Ile
130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg Ser Xaa Cys Cys His
        275                 280

<210> SEQ ID NO 10
<211> LENGTH: 285
<212> TYPE: PRT
<213> ORGANISM: Homo sapiens
<220> FEATURE:
<221> NAME/KEY: UNSURE
<222> LOCATION: (1)..(285)
<223> OTHER INFORMATION: Xaa or single letter X represents
      Selenocystein (U) in originally disclosed sequence

<400> SEQUENCE: 10

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
            20                  25                  30

Val Ala Leu Leu Gln Ala Ser Xaa Tyr Leu Cys Ile Leu Gln Ala Ser
         35                  40                  45

Lys Leu Glu Asp Leu Arg Val Lys Leu Lys Lys Glu Gly Tyr Ser Asn
 50                  55                  60

Ile Ser Tyr Ile Val Val Asn His Gln Gly Ile Ser Ser Arg Leu Lys
 65                  70                  75                  80

Tyr Thr His Leu Lys Asn Lys Val Ser Glu His Ile Pro Val Tyr Gln
                 85                  90                  95

Gln Glu Glu Asn Gln Thr Asp Val Trp Thr Leu Leu Asn Gly Ser Lys
             100                 105                 110

Asp Asp Phe Leu Ile Tyr Asp Arg Cys Gly Arg Leu Val Tyr His Leu
         115                 120                 125

Gly Leu Pro Phe Ser Phe Leu Thr Phe Pro Tyr Val Glu Glu Ala Ile
    130                 135                 140

Lys Ile Ala Tyr Cys Glu Lys Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
        195                 200                 205

Gln Pro Gly Ala Pro Asn Ala Pro Thr His Pro Ala Pro Pro Gly Leu
    210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg Ser Xaa Cys Cys His Cys
        275                 280                 285

<210> SEQ ID NO 11
<211> LENGTH: 286
<212> TYPE: PRT
<213> ORGANISM: Homo sapiens
<220> FEATURE:
<221> NAME/KEY: UNSURE
<222> LOCATION: (1)..(286)
<223> OTHER INFORMATION: Xaa or single letter X represents
      Selenocystein (U) in originally disclosed sequence

<400> SEQUENCE: 11

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
                20                  25                  30

Val Ala Leu Leu Gln Ala Ser Xaa Tyr Leu Cys Ile Leu Gln Ala Ser
         35                  40                  45

Lys Leu Glu Asp Leu Arg Val Lys Leu Lys Lys Glu Gly Tyr Ser Asn
 50                  55                  60

Ile Ser Tyr Ile Val Val Asn His Gln Gly Ile Ser Ser Arg Leu Lys
 65                  70                  75                  80

Tyr Thr His Leu Lys Asn Lys Val Ser Glu His Ile Pro Val Tyr Gln
                 85                  90                  95

```
Gln Glu Glu Asn Gln Thr Asp Val Trp Thr Leu Leu Asn Gly Ser Lys
                100                 105                 110

Asp Asp Phe Leu Ile Tyr Asp Arg Cys Gly Arg Leu Val Tyr His Leu
            115                 120                 125

Gly Leu Pro Phe Ser Phe Leu Thr Phe Pro Tyr Val Glu Glu Ala Ile
130                 135                 140

Lys Ile Ala Tyr Cys Glu Lys Cys Gly Asn Cys Ser Leu Thr Thr
145                 150                 155                 160

Leu Lys Asp Glu Asp Phe Cys Lys Arg Val Ser Leu Ala Thr Val Asp
                165                 170                 175

Lys Thr Val Glu Thr Pro Ser Pro His Tyr His Glu His His His
            180                 185                 190

Asn His Gly His Gln His Leu Gly Ser Ser Glu Leu Ser Glu Asn Gln
            195                 200                 205

Gln Pro Gly Ala Pro Asn Ala Pro Thr His Pro Ala Pro Pro Gly Leu
            210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
            260                 265                 270

Asp Ser Glu Leu Ala Pro Arg Ser Xaa Cys Cys His Cys Arg
            275                 280                 285

<210> SEQ ID NO 12
<211> LENGTH: 287
<212> TYPE: PRT
<213> ORGANISM: Homo sapiens
<220> FEATURE:
<221> NAME/KEY: UNSURE
<222> LOCATION: (1)..(287)
<223> OTHER INFORMATION: Xaa or single letter X represents
      Selenocystein (U) in originally disclosed sequence

<400> SEQUENCE: 12

Glu Ser Gln Asp Gln Ser Ser Leu Cys Lys Gln Pro Pro Ala Trp Ser
1               5                   10                  15

Ile Arg Asp Gln Asp Pro Met Leu Asn Ser Asn Gly Ser Val Thr Val
                20                  25                  30

Val Ala Leu Leu Gln Ala Ser Xaa Tyr Leu Cys Ile Leu Gln Ala Ser
            35                  40                  45

Lys Leu Glu Asp Leu Arg Val Lys Leu Lys Lys Glu Gly Tyr Ser Asn
50                  55                  60

Ile Ser Tyr Ile Val Val Asn His Gln Gly Ile Ser Ser Arg Leu Lys
65                  70                  75                  80

Tyr Thr His Leu Lys Asn Lys Val Ser Glu His Ile Pro Val Tyr Gln
                85                  90                  95

Gln Glu Glu Asn Gln Thr Asp Val Trp Thr Leu Leu Asn Gly Ser Lys
                100                 105                 110

Asp Asp Phe Leu Ile Tyr Asp Arg Cys Gly Arg Leu Val Tyr His Leu
            115                 120                 125

Gly Leu Pro Phe Ser Phe Leu Thr Phe Pro Tyr Val Glu Glu Ala Ile
130                 135                 140

Lys Ile Ala Tyr Cys Glu Lys Lys Cys Gly Asn Cys Ser Leu Thr Thr
145                 150                 155                 160
```

-continued

```
Leu Lys Asp Glu Asp Phe Cys Lys Arg Val Ser Leu Ala Thr Val Asp
            165                 170                 175

Lys Thr Val Glu Thr Pro Ser Pro His Tyr His His Glu His His His
            180                 185                 190

Asn His Gly His Gln His Leu Gly Ser Ser Glu Leu Ser Glu Asn Gln
            195                 200                 205

Gln Pro Gly Ala Pro Asn Ala Pro Thr His Pro Ala Pro Pro Gly Leu
            210                 215                 220

His His His His Lys His Lys Gly Gln His Arg Gln Gly His Pro Glu
225                 230                 235                 240

Asn Arg Asp Met Pro Ala Ser Glu Asp Leu Gln Asp Leu Gln Lys Lys
                245                 250                 255

Leu Cys Arg Lys Arg Cys Ile Asn Gln Leu Leu Cys Lys Leu Pro Thr
                260                 265                 270

Asp Ser Glu Leu Ala Pro Arg Ser Xaa Cys Cys His Cys Arg His
            275                 280                 285

<210> SEQ ID NO 13
<211> LENGTH: 235
<212> TYPE: PRT
<213> ORGANISM: Homo sapiens
<220> FEATURE:
<221> NAME/KEY: UNSURE
<222> LOCATION: (1)..(235)
<223> OTHER INFORMATION: Xaa or single letter X represents
      Selenocystein (U) in originally disclosed sequence

<400> SEQUENCE: 13

Met Trp Arg Ser Leu Gly Leu Ala Leu Ala Leu Cys Leu Leu Pro Ser
1               5                   10                  15

Gly Gly Thr Glu Ser Gln Asp Gln Ser Ser Leu Cys Lys Gln Pro Pro
            20                  25                  30

Ala Trp Ser Ile Arg Asp Gln Asp Pro Met Leu Asn Ser Asn Gly Ser
        35                  40                  45

Val Thr Val Val Ala Leu Leu Gln Ala Ser Xaa Tyr Leu Cys Ile Leu
    50                  55                  60

Gln Ala Ser Lys Leu Glu Asp Leu Arg Val Lys Leu Lys Lys Glu Gly
65                  70                  75                  80

Tyr Ser Asn Ile Ser Tyr Ile Val Val Asn His Gln Gly Ile Ser Ser
                85                  90                  95

Arg Leu Lys Tyr Thr His Leu Lys Asn Lys Val Ser Glu His Ile Pro
            100                 105                 110

Val Tyr Gln Gln Glu Glu Asn Gln Thr Asp Val Trp Thr Leu Leu Asn
            115                 120                 125

Gly Ser Lys Asp Asp Phe Leu Ile Tyr Asp Arg Cys Gly Arg Leu Val
        130                 135                 140

Tyr His Leu Gly Leu Pro Phe Ser Phe Leu Thr Phe Pro Tyr Val Glu
145                 150                 155                 160

Glu Ala Ile Lys Ile Ala Tyr Cys Glu Lys Lys Cys Gly Asn Cys Ser
                165                 170                 175

Leu Thr Thr Leu Lys Asp Glu Asp Phe Cys Lys Arg Val Ser Leu Ala
            180                 185                 190

Thr Val Asp Lys Thr Val Glu Thr Pro Ser Pro His Tyr His His Glu
        195                 200                 205

His His His Asn His Gly His Gln His Leu Gly Ser Ser Glu Leu Ser
    210                 215                 220
```

```
Glu Asn Gln Gln Pro Gly Ala Pro Asn Ala Pro
225                 230                 235

<210> SEQ ID NO 14
<211> LENGTH: 103
<212> TYPE: PRT
<213> ORGANISM: Homo sapiens
<220> FEATURE:
<221> NAME/KEY: UNSURE
<222> LOCATION: (1)..(103)
<223> OTHER INFORMATION: Xaa or single letter X represents
      Selenocystein (U) in originally disclosed sequence

<400> SEQUENCE: 14

Lys Arg Cys Ile Asn Gln Leu Leu Cys Lys Leu Pro Thr Asp Ser Glu
1               5                   10                  15

Leu Ala Pro Arg Ser Xaa Cys Cys His Cys Arg His Leu Ile Phe Glu
                20                  25                  30

Lys Thr Gly Ser Ala Ile Thr Xaa Gln Cys Lys Glu Asn Leu Pro Ser
            35                  40                  45

Leu Cys Ser Xaa Gln Gly Leu Arg Ala Glu Glu Asn Ile Thr Glu Ser
    50                  55                  60

Cys Gln Xaa Arg Leu Pro Pro Ala Ala Xaa Gln Ile Ser Gln Gln Leu
65                  70                  75                  80

Ile Pro Thr Glu Ala Ser Ala Ser Xaa Arg Xaa Lys Asn Gln Ala Lys
                85                  90                  95

Lys Xaa Glu Xaa Pro Ser Asn
            100

<210> SEQ ID NO 15
<211> LENGTH: 70
<212> TYPE: PRT
<213> ORGANISM: Homo sapiens
<220> FEATURE:
<221> NAME/KEY: UNSURE
<222> LOCATION: (1)..(70)
<223> OTHER INFORMATION: Xaa or single letter X represents
      Selenocystein (U) in originally disclosed sequence

<400> SEQUENCE: 15

Thr Gly Ser Ala Ile Thr Xaa Gln Cys Lys Glu Asn Leu Pro Ser Leu
1               5                   10                  15

Cys Ser Xaa Gln Gly Leu Arg Ala Glu Glu Asn Ile Thr Glu Ser Cys
                20                  25                  30

Gln Xaa Arg Leu Pro Pro Ala Ala Xaa Gln Ile Ser Gln Gln Leu Ile
            35                  40                  45

Pro Thr Glu Ala Ser Ala Ser Xaa Arg Xaa Lys Asn Gln Ala Lys Lys
        50                  55                  60

Xaa Glu Xaa Pro Ser Asn
65                  70
```

SELENOPROTEIN P FOR PREDICTION OF A FIRST CARDIOVASCULAR EVENT Subject of the present invention is a method for assessing a risk for getting a first cardiovascular event or assessing the risk for cardiovascular mortality in a subject, comprising
  a) determining the level and/or the amount of Selenoprotein P and/or fragments thereof in a sample of said subject
  b) correlating the determined level and/or the amount of Selenoprotein P and/or fragments thereof with the risk for getting a first cardiovascular event or assessing the risk for cardiovascular mortality in said subject.

Selenoprotein P (abbreviations Sepp1, SeP, SELP, SePP) is a plasma selenoprotein, that serve as selenium nutritional marker and its plasma concentration fall as the severity of selenium deficiency increases (Yang et al. 1989. *J Nutr* 119:1010-1012; Renko et al. 2008. *Biochem J* 409:741-749).

Because selenium functions through selenoproteins, it has been proposed that optimum health would be achieved if enough of the element were supplied to prevent selenium from becoming the limiting factor in selenoprotein synthesis. Determination of selenoprotein optimization has become the major technique used to assess the selenium nutritional requirement (Burk and Hill 2009. *Biochim Biophys Acta.* 1790(11): 1441-1447).

So far, over 25 selenoproteins have been identified that play diverse roles in the regulation of cellular redox processes (Liu et al. 2017. *Metallomics* 9: 21-37). They are expressed in a variety of tissues and cells and exhibit numerous functions, e.g. glutathione peroxidases (GPx) detoxify intracellular hydrogen peroxide thus protecting the cell from lipoprotein and/or DNA damage while thioredoxin reductases (TrxR) regenerate thioredoxin and thereby balance the redox status of the cell (Reeves and Hoffmann 2009. *Cell. Mol. Life Sci.* 66, 2457-2478).

Selenium plays an essential part in the selenoprotein-induced defense system. Consequently, selenium blood levels have been widely utilized as a biomarker for oxidative stress-associated diseases. Various observational studies have investigated the significance of serum selenium levels on the development of cardiovascular diseases with conflicting results. A dietary supplementation trial with selenium in healthy elderly subjects showed that the cardiovascular mortality was significantly reduced and the cardiac function significantly improved (Alehagen et al. 2013. *Int J Cardiol* 167(5): 1860-1866) and this was still observed during a follow-up time of 10 years after intervention (Alehagen and Johansson 2015. *PLoS One* 10(12): e0141641). Moreover, low selenium concentration was associated with future cardiovascular death in patients with acute coronary syndrome (ACS) but not in patients with stable angina pectoris (Lubos et al. 2010. *Atherosclerosis* 209: 271-277). In contrast, meta-analyses of several selenium supplementation trials reported that there were no statistically significant effects of selenium supplementation on cardiovascular mortality and all fatal and non-fatal cardiovascular disease events (Flores-Mateo et al. 2006. *Am J Clin Nutr* 84: 762-773; Rees et al. 2013. *Cochrane Database Syst Rev* CD009671). In summary, the results from randomized trials to date have been inconsistent and the role of Se supplementation in CVD prevention is inconclusive. The difference in the baseline selenium status of the populations studied and the dose of selenium supplementation might partially account for the lack of consistency in trial studies. Selenium supplementation may benefit people with low baseline selenium status, but have no effect or even an adverse effect on the cardiovascular system in people with adequate-to-high status. For example, supplementation of additional selenium in people who already have adequate selenium intake might increase their risk of type-2 diabetes (Rayman and Stranges 2013. *Free Radical Biol Med* 65: 1557-1564). Thus, a U-shaped association between selenium status and CVD risk may be reasonable (Bleys et al. 2008. *Arch Intern Med* 168: 404-410).

Selenium supplementation studies (Meplan et al. 2007. *FASEB J* 21: 3063-3074; Xia et al. 2005. *Am J Clin Nutr* 81:829-834; Burk et al. 2006. *Cancer Epidemiol Biomarkers Prev* 15: 804-810) indicate that SePP plasma concentration is the best easily accessible marker of human selenium nutritional status. Once the nutritional requirement has been met, however, SePP concentration does not reflect additional increases in selenium intake.

Selenoprotein P is a secreted glycoprotein that contains most of the selenium in plasma (Hill et al. 1996. *J Nutr* 126: 138-145; Read et al. 1990. *J Biol Chem* 265: 17899-17905). With respect to its selenium content, SePP can be divided into two domains. The N-terminal domain, approximately two-thirds of the amino acid sequence, contains 1 selenocysteine (U) in a U-x-x-C redox motif. The shorter C-terminal domain contains multiple selenocysteines, e.g. 9 in rats, mice, and humans.

Full-length SePP is present in plasma but so are shortened forms that have reduced selenium content. SePP purified from rat plasma is present as 4 isoforms. In addition to the full-length isoform that contains 10 selenocysteine residues, shorter isoforms are present that terminate at the second, third, and seventh selenocysteine positions. These isoforms contain 1, 2, and 6 selenocysteine residues, respectively (Himeno et al. 1996. *J Biol Chem* 271: 15769-157759; Ma et al. 2002. *J Biol Chem* 277: 12749-12754). There is evidence for the existence of SePP isoforms in the mouse (Hill et al. 2007. *J Biol Chem* 282: 10972-1098) and the human (Akesson et al. 1994. *Biochim Biophys Acta* 1204: 243-249), respectively. Structurally, human SePP is a protein containing 381 amino acid residues (SEQ ID No. 1) of which ten are predicted to be Sec residues at positions 59, 300, 318, 330, 345, 352, 367, 369, 376 and 378.

Its secreted form (after cleavage of the signal sequence) contains 362 amino acid residues (SEQ ID NO. 2) and may contain post-translational modifications, which can include phosphorylation and multiple sites of glycosylation. Moreover, several fragments including fragments containing the N- or C-terminal part of SePP have been identified (Ballihaut et al. 2012. *Metallomics* 4: 533-538; Hirashima et al. 2003. *Biol Pharm Bull* 26(6): 794-798).

The liver produces most of the SePP in plasma, where its turnover is rapid. SePP is also expressed in other tissues and is presumably secreted by them (Hill et al. 1993. *Proc Natl Acad Sci USA* 90:537-541; Yang et al. 2000. *Biochim Biophys Acta* 1474: 390-396). The liver acquires selenium from several sources and apportions it between selenoprotein synthesis and excretion from the organism. Specifically, liver synthesizes its intrinsic selenoproteins as well as the secreted selenium molecules SePP and excretory metabolites. Whole-body selenium, thus, appears to be regulated in the liver by the distribution of metabolically available selenium between the pathways of selenoprotein synthesis and selenium excretory metabolite synthesis.

Elevated circulating selenoprotein P concentrations have been reported in patients with T2DM and prediabetes and were associated shown to be related to atherosclerosis (Yang, et al. 2011. *J. Clin. Endocrinol. Metab.* 96: E1325-E1329). Moreover, SePP concentrations were increased in overweight and obese patients (Chen et al. 2017. *Obes Res Clin Pract* 11(2): 227-232). In contrast, SePP concentration is decreased in sepsis and is presumably the cause of the decline in selenium concentration (Hollenbach et al. 2008. *Journal of Trace Elements in Medicine and Biology* 22: 24-32) or a decreased release of it by the liver (Renko et al. 2009. *FASEB J* 23:1758-1765). Significantly decreased circulating SePP levels that were associated to the metabolic syndrome status were also found in patients with documented cardiovascular disease (Gharipour et al. 2017. *J Gene Med* 19:e2945).

A highly significant correlation was found between the serum selenium and selenoprotein-P levels (Andoh et al. 2005. *Nutrition* 21(5): 574-9).

Several SePP quantification methods by antibody-based assays are known: a radioimmunoassay (Hill et al. 1996. *J Nutr* 126:138-45), an enzyme-linked immunosorbent assay (Andoh et al. 2005. *Nutrition* 21(5):574-9), a very sensitive chemiluminescence immunoassay (Hollenbach et al. 2008. *Journal of Trace Elements in Medicine and Biology* 22: 24-32) and very recently sandwich SELENOP-ELISA that was calibrated against a standard reference material (Hybsier et al. 2017. *Redox Biology* 11: 403-414).

An increased risk for all cause mortality in patients with mainly diabetes exhibiting decreases plasma SePP-values has been described in WO2015/185672.

A subject of the present invention was to investigate the prognostic and diagnostic power of SePP for predicting the risk of getting a first cardiovascular event (including cardiovascular mortality) in a healthy subject. To address this issue, we measured SePP in a Swedish prospective cohort study (Malmo Preventive Project (MPP)). And related baseline level of this biomarker to first cardiovascular events (including cardiovascular death) during 10 years of follow-up.

Surprisingly, it has been shown that selenoprotein P and/or fragments thereof is a powerful and highly significant biomarker for predicting the risk of getting a first cardiovascular event or cardiovascular mortality, especially in smokers.

Subject of the present invention is a method for assessing a risk for getting a first cardiovascular event or assessing the risk for cardiovascular mortality in a subject, comprising
  a) determining the level and/or the amount of Selenoprotein P and/or fragments thereof in a sample of said subject
  b) correlating the determined level and/or the amount of Selenoprotein P and/or fragments thereof with the risk for getting a first cardiovascular event or assessing the risk for cardiovascular mortality in said subject.

Subject of the present invention is a method for assessing a risk for getting a first cardiovascular event or assessing the risk for cardiovascular mortality in a subject as defined above wherein the risk for getting a first cardiovascular event or assessing the risk for cardiovascular mortality is enhanced when the determined level and/or the amount of Selenoprotein P and/or fragments thereof in a sample of said subject is below a threshold.

Subject of the present invention is a method for assessing a risk for getting a first cardiovascular event or assessing the risk for cardiovascular mortality in a subject as defined above wherein the risk for getting a first cardiovascular event or assessing the risk for cardiovascular mortality is enhanced when said level and/or the amount of Selenoprotein P and/or fragments thereof in said sample is below a threshold wherein said threshold is between 4.0 and 5.5 mg/L.

The term "subject" as used herein refers to a living human or non-human organism. Preferably herein the subject is a human subject. The subject may be healthy or diseased if not stated otherwise.

In one embodiment said subject does not take statins or is not undergoing a treatment with statins.

The term "decreased level" means a level below a certain threshold level. The term "increased level" means a level above a certain threshold level.

A bodily fluid may be selected from the group comprising blood, serum, plasma, urine, cerebrospinal liquid (CSF), and saliva.

The term "determining the level of Selenoprotein P", means that usually the immunoreactivity towards a region within the before mentioned molecules is determined. This means that it is not necessary that a certain fragment is measured selectively. It is understood that a binder which is used for the determination of the level of Selenoprotein P and/or fragments thereof binds to any fragment that comprises the region of binding of said binder. Said binder may be an antibody or antibody fragment or a non-IgG Scaffold.

In one specific embodiment the level of Selenoprotein P is measured with an immunoassay and said binder is an antibody, or an antibody fragment binding to Selenoprotein P and/or fragments thereof.

A variety of immunoassays are known and may be used for the assays and methods of the present invention, these include: radioimmunoassays ("RIA"), homogeneous enzyme-multiplied immunoassays ("EMIT"), enzyme linked immunoadsorbent assays ("ELISA"), apoenzyme reactivation immunoassay ("ARIS"), chemiluminescence- and fluorescence-immunoassays, Luminex-based bead arrays, protein microarray assays, and rapid test formats such as for instance immunochromatographic strip tests ("dipstick immunoassays") and immuno-chromatography assays.

In one embodiment of the invention such an assay is a sandwich immunoassay using any kind of detection technology including but not restricted to enzyme label, chemiluminescence label, electrochemiluminescence label, preferably a fully automated assay. In one embodiment of the invention such an assay is an enzyme labeled sandwich assay. Examples of automated or fully automated assay comprise assays that may be used for one of the following systems: Roche Elecsys®, Abbott Architect®, Siemens Centauer®, Brahms Kryptor®, Biomerieux Vidas®, Alere Triage®.

In one embodiment of the invention it may be a so-called POC-test (point-of-care) that is a test technology which allows performing the test within less than 1 hour near the patient without the requirement of a fully automated assay system. One example for this technology is the immunochromatographic test technology.

In one embodiment of the invention at least one of said two binders is labeled in order to be detected.

In a preferred embodiment said label is selected from the group comprising chemiluminescent label, enzyme label, fluorescence label, radioiodine label.

The assays can be homogenous or heterogeneous assays, competitive and non-competitive assays. In one embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook, Ed.* David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134).

In another embodiment the assay comprises two capture molecules, preferably antibodies which are both present as dispersions in a liquid reaction mixture, wherein a first labelling component is attached to the first capture molecule, wherein said first labelling component is part of a labelling system based on fluorescence- or chemiluminescence-quenching or amplification, and a second labelling component of said marking system is attached to the second capture molecule, so that upon binding of both capture molecules to the analyte a measurable signal is generated that allows for the detection of the formed sandwich complexes in the solution comprising the sample.

In another embodiment, said labeling system comprises rare earth cryptates or rare earth chelates in combination with fluorescence dye or chemiluminescence dye, in particular a dye of the cyanine type.

In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in (Kirk-Othmer, *Encyclopedia of chemical technology, 4th ed.*, executive editor, J. I. Kroschwitz; editor, M. Howe-Grant, John Wiley & Sons, 1993, vol. 15, p. 518-562, incorporated herein by reference, including citations on pages 551-562). Chemiluminescent label may be acridinium ester label, steroid labels involving isoluminol labels and the like. Preferred chemiluminescent dyes are acridiniumesters.

Enzyme labels may be lactate dehydrogenase (LDH), creatine kinase (CPK), alkaline phosphatase, aspartate aminotransferase (AST), alanine aminotransferase (ALT), acid phosphatase, glucose-6-phosphate dehydrogenase and so on.

In one embodiment of the assays for determining Selenoprotein P and/or fragments thereof in a sample according to the present invention the assay sensitivity of said assay is <0.100 mg/L, preferably <0.05 mg/L and more preferably <0.01 mg/L.

According to the invention the diagnostic binder to Selenoprotein P and/or fragments thereof is selected from the group consisting of antibodies e.g. IgG, a typical full-length immunoglobulin, or antibody fragments containing at least the F-variable domain of heavy and/or light chain as e.g. chemically coupled antibodies (fragment antigen binding) including but not limited to Fab-fragments including Fab minibodies, single chain Fab antibody, monovalent Fab antibody with epitope tags, e.g. Fab-V5Sx2; bivalent Fab (mini-antibody) dimerized with the $CH_3$ domain; bivalent Fab or multivalent Fab, e.g. formed via multimerization with the aid of a heterologous domain, e.g. via dimerization of dHLX domains, e.g. Fab-dHLX-FSx2; F(ab')2-fragments, scFv-fragments, multimerized multivalent or/and multispecific scFv-fragments, bivalent and/or bispecific diabodies, BITE® (bispecific T-cell engager), trifunctional antibodies, polyvalent antibodies, e.g. from a different class than G; single-domain antibodies, e.g. nanobodies derived from camelid or fish immunoglobulines.

In a specific embodiment the level of Selenoprotein P and/or fragments thereof are measured with an assay using binders selected from the group comprising an antibody, an antibody fragment, aptamers, non-Ig scaffolds as described in greater detail below binding to Selenoprotein P and/or fragments thereof.

As mentioned herein, an "assay" or "diagnostic assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is greater than $10^7$ $M^{-1}$, preferred $10^8$ $M^{-1}$, more preferred greater than $10^9$ $M^{-1}$, most preferred greater than $10^{10}$ $M^{-1}$. Binding affinity may be determined using the Biacore method, offered as service analysis e.g. at Biaffin, Kassel, Germany (http://www.biaffin.com/de/).

In the context of the present invention, "binder molecules" are molecules which may be used to bind target molecules or molecules of interest, i.e. analytes (i.e. in the context of the present invention Selenoprotein P and fragments thereof), from a sample. Binder molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, binder molecules may for instance be selected from the group comprising a nucleic acid molecule, a carbohydrate molecule, a PNA molecule, a protein, an antibody, a peptide or a glycoprotein. Preferably, the binder molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

In addition to antibodies other biopolymer scaffolds are well known in the art to complex a target molecule and have been used for the generation of highly target specific biopolymers. Examples are aptamers, spiegelmers, anticalins and conotoxins. Non-Ig scaffolds may be protein scaffolds and may be used as antibody mimics as they are capable to bind to ligands or antigens. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds (e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins preferably microproteins forming a cystine knot) scaffolds (e.g. described in EP 2314308), Fyn $SH_3$ domain based scaffolds (e.g. described in WO 2011/023685) EGFR-A-domain based scaffolds (e.g. described in WO 2005/040229) and Kunitz domain based scaffolds (e.g. described in EP 1941867).

In one embodiment of the invention at least one of said two binders is bound to a solid phase as magnetic particles, and polystyrene surfaces.

Alternatively, the level of any of the above analytes may be determined by other analytical methods e.g. mass spectroscopy.

In one specific embodiment of the method according to the invention said subject has never had a cardiovascular event and has never had any cardiovascular disease. In another specific embodiment of the method according to the invention said subject has carotid plaque but no symptoms of carotid artery disease. An established method to detect the presence of an atherosclerotic disease and to monitor its regression, arrest or progression is the measurement of the intima-media thickness (IMT) (de Groot et al. 2008. *Nature Reviews Cardiology* 5, 280-288). This is a measurement of the thickness of tunica intima and tunica media, the innermost two layers of the wall of an artery. The measurement is usually made by external ultrasound and occasionally by internal, invasive ultrasound catheters. The FDA has approved IMT as a surrogate marker of atherosclerotic disease for application in clinical trials. The extent of IMT has been associated with cardiovascular outcome and its change of over time (statistically significant of IMT per year) with efficacy of drugs (de Groot et al. 2008. *Nature Reviews Cardiology* 5; Hedblad et al. 2001. *Circulation* 103:1721-1726).

In another specific embodiment of the invention at the time the sample of bodily fluid is taken from said subject, said subject has no predisposition for cardiovascular diseases, e.g. no pre-diabetes, impaired fasting glucose or diabetes mellitus.

Said cardiovascular event or cardiovascular disease may be selected from the group comprising heart failure, atherosclerosis, hypertension, cardiomyopathy, myocardial infarction and stroke. Said cardiovascular event or cardiovascular disease may be selected from the group comprising myocardial infarction, acute heart failure, stroke and said cardiovascular mortality is selected from cardiovascular death related to myocardial infarction, stroke or acute heart failure.

In one embodiment, said cardiovascular event or cardiovascular disease may be selected from the group comprising heart failure, atherosclerosis, hypertension, cardiomyopathy and myocardial infarction. Said cardiovascular event or cardiovascular disease may be selected from the group comprising myocardial infarction, acute heart failure, and said cardiovascular mortality is selected from cardiovascular death related to myocardial infarction, or acute heart failure.

In one embodiment, said cardiovascular event or cardiovascular disease may be selected from the group comprising heart failure, atherosclerosis, hypertension, cardiomyopathy and myocardial infarction, but said cardiovascular event or cardiovascular disease is not stroke. Said cardiovascular event or cardiovascular disease may be selected from the group comprising myocardial infarction, acute heart failure, but said cardiovascular event or cardiovascular disease is not stroke, and said cardiovascular mortality is selected from cardiovascular death related to myocardial infarction, or acute heart failure, but said cardiovascular mortality is not related to stroke.

In one embodiment of the method according to the invention said method is used for prevention of a first cardiovascular event or prevention of a cardiovascular disease.

In one embodiment of the method according to the invention said method is used for prevention of a first cardiovascular event, which is not stroke, or prevention of a cardiovascular disease, which is not stroke.

In a specific embodiment of the invention said first cardiovascular event is an acute cardiovascular event selected from the group comprising myocardial infarction, acute heart failure, stroke, coronary re-vascularization and cardiovascular death related to myocardial infarction, stroke or acute heart failure.

In a specific embodiment of the invention said first cardiovascular event is an acute cardiovascular event selected from the group comprising myocardial infarction, acute heart failure, coronary re-vascularization and cardiovascular death related to myocardial infarction, or acute heart failure.

In a specific embodiment of the invention said first cardiovascular event is an acute cardiovascular event selected from the group comprising myocardial infarction, acute heart failure, coronary re-vascularization, but not stroke, and cardiovascular death related to myocardial infarction, or acute heart failure, but not related to stroke.

In one embodiment of the invention said subject is a current smoker or a former smoker (who has smoked in the past, e.g. several weeks ago or several months ago or several years ago). A smoker is defined as a subject who is smoking e.g. cigarettes on a regular basis (including occasional smoking like social smoking or some-day smoking).

Risk of a first cardiovascular event or cardiovascular mortality means the risk of getting an event due to cardiovascular reasons or the risk of dying because of cardiovascular reasons within a certain period of time. In a specific embodiment said period of time is within 10 years, or within 8 years, or within 5 years or within 2.5 years.

Risk of a first cardiovascular event or cardiovascular mortality means the risk of getting an event due to cardiovascular reasons or the risk of dying because of cardiovascular reasons within a certain period of time, but wherein the first cardiovascular event or cardiovascular mortality is not stroke or related to stroke. In a specific embodiment said period of time is within 10 years, or within 8 years, or within 5 years or within 2.5 years.

The definition of diabetes is as follows: a history of physician diagnosis or being on anti-diabetic medication or having a fasting whole blood glucose >1=6.1 mmol/l (note this is =7.0 mmol/l in plasma) at the baseline examination.

Pre-diabetes or impaired fasting glucose (IFG) is defined as whole blood fasting plasma glucose between >1=5.4 and <6.1 mmol/l (which corresponds to 6.1-6.9 mmol/l in plasma).

In a specific embodiment of the method according to the invention said subject is a non-diabetic subject with fasting whole blood glucose of less than 5.4 mmol/l (which corresponds to <6.1 mmol/l in plasma).

The definition of normotensive/high blood pressure (HBP) is as follows:

HBP is defined as systolic BP>1=140 mmHg, diastolic BP>1=90 mmHg or being on anti-hypertensive medications. Subjects having normal blood pressure are all other subjects, i.e. subjects with systolic BP<140 mmHg or diastolic BP<90 mmHg or not being on anti-hypertensive medications.

In another embodiment at least one clinical parameter is additionally determined wherein said clinical parameter is selected from the group comprising: age, presence of diabetes mellitus, current smoking, systolic blood pressure, diastolic blood pressure, body mass index (BMI), anti-hypertensive treatment, waist-to-hip ratio, waist circumference.

In a specific embodiment of the methods of the present invention additionally at least one further biomarker is determined in the bodily fluid of said subject and correlated with said risk of getting a first cardiovascular event, wherein said additional biomarker is selected from the group comprising: pro-Neurotensin 1-117 (PNT 1-117), C-reactive protein (CRP), pro-brain natriuretic peptide 1-108 (proBNP 1-108), proBNP, BNP, pro-atrial natriuretic peptide 1-98 (proANP-N-terminal fragment), pro-ANP and fragments thereof of at least 5 amino acids in length, adrenomedullin, pro-adrenomedullin (proADM) and fragments thereof of at least 5 amino acids in length, ST-2, GDF15, Galectin-3, copeptin, human growth hormone (hGH), fasting blood or plasma glucose, triglycerides, HDL cholesterol or subfractions thereof, LDL cholesterol or subfractions thereof, Insulin, Cystatin C.

Subject matter of the present invention is also a method for determining the risk of getting a first cardiovascular event or cardiovascular death as defined in any of the preceding paragraphs, wherein said method is performed in order to stratify said subjects into risk groups as further defined below. In specific embodiments of the invention the methods are used in order to stratify the subjects into risk groups, e.g. those with a low risk, medium risk, or high risk to get a first cardiovascular event or cardiovascular death. Low risk of getting a first cardiovascular event or cardiovascular death means that the value of selenoprotein P and/or fragments thereof is substantially not decreased compared to a predetermined value in healthy subjects who did not get a first cardiovascular event or cardiovascular death. A medium risk exists when the level of selenoprotein P and/or fragments thereof is elevated compared to a predetermined value in healthy subjects who did not get a first cardiovascular event or cardiovascular death, and a high risk exists when the level of selenoprotein P and/or fragments thereof is significantly decreased at baseline measurement and continues to decrease at subsequent analysis.

Fragments of Selenoprotein P may be selected from the group comprising SEQ ID No. 3 to 15.

The threshold for determining the risk of getting a first cardiovascular event or cardiovascular death may be the lower normal range of a healthy population e.g. the median 5.5 mg/L, more preferred 5.0 mg/L, even more preferred 4.5 mg/L, most preferred 4.0 mg/L. A threshold range is useful between 4.0 and 5.5 mg/L. These thresholds are related to the calibration method mentioned in the examples.

All thresholds and values have to be seen in correlation to the test and the calibration used according to the Examples. A person skilled in the art may know that the absolute value of a threshold might be influenced by the calibration used. This means that all values and thresholds given herein are to be understood in context of the calibration used.

Threshold levels may be determined by measuring samples from subjects who did develop a certain condition (e.g. a cardiovascular event) and samples from subjects who did not develop the condition. One possibility to determine a threshold is the calculation of receiver operating characteristic curves (ROC curves), plotting the value of a variable versus its relative frequency in the "normal" population (e.g. subjects who did not develop the condition) and "disease" population (e.g. subjects who did develop the condition). A distribution of the marker levels for subjects developing or not developing a certain condition will likely overlap. Under such conditions, a test does not absolutely distinguish "normal" from "disease" with 100% accuracy, and the area of overlap indicates where the test cannot distinguish normal from "disease". A threshold is selected, above which (or below which, depending on how a marker changes with the "disease") the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (Hanley et al. 1982. *Radiology* 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement. The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test. The odds ratio is a measure of effect size, describing the strength of association or non-independence between two binary data values (e.g. the ratio of the odds of an event occurring in test negative group to the odds of it occurring in the test positive group).

Threshold levels can be obtained for instance from a Kaplan-Meier analysis, where the occurrence of a disease or the probability of a serious condition and/or death is correlated with the e.g. quartiles of the respective markers in the population. According to this analysis, subjects with marker levels above the 75th percentile have a significantly increased risk for getting the diseases according to the invention. This result is further supported by Cox regression analysis with adjustment for classical risk factors. The highest (or lowest quartile, depending on how a marker changes with the "disease") versus all other subjects is highly significantly associated with increased risk for getting a disease or the probability of a serious condition and/or death according to the invention.

Other preferred cut-off values are for instance the 10th, 5th or 1st percentile of a reference population. By using a higher percentile than the 25th percentile, one reduces the number of false positive subjects identified, but one might miss to identify subjects, who are at moderate, albeit still increased risk. Thus, one might adapt the cut-off value depending on whether it is considered more appropriate to identify most of the subjects at risk at the expense of also identifying "false positives", or whether it is considered more appropriate to identify mainly the subjects at high risk at the expense of missing several subjects at moderate risk.

The person skilled in the art knows how to determine such statistically significant levels.

Subject matter of the present invention is also a method for determining the risk of getting a first cardiovascular event or cardiovascular death in any of the preceding paragraphs, wherein said method is performed more than once in order to monitor the risk of getting a first cardiovascular event or cardiovascular death. Said monitoring may be performed in order to evaluate the response of said subject to preventive and/or therapeutic measures taken using the measurement of selenoprotein P and/or fragments thereof.

In one embodiment of the invention the sample is selected from the group comprising whole blood, plasma, and serum.

A preventive therapy or intervention is the supplementation with selenium. Selenium may be applied as selenite, selenate or selenomethionine (L-selenomethionine).

The supplementation with selenium may be applied in combination with vitamins (e.g. vitamin E, vitamin C, vitamin A) and/or mineral nutrients (e.g. iodine, fluoride, zinc) and/or co-factors (e.g. coenzyme Q10).

Myocardial infarction (MI), commonly known as a heart attack, occurs when blood flow decreases or stops to a part of the heart, causing damage to the heart muscle. The most common symptom is chest pain or discomfort, which may travel into the shoulder, arm, back, neck, or jaw. Myocardial infarction can be divided into ST-segment elevation myocardial infarction (STEMI) or non-ST-segment elevation myocardial infarction (NSTEMI).

Heart failure (HF) is a cardiac condition that occurs, when a problem with the structure or function of the heart impairs its ability to supply sufficient blood flow to meet the body's needs. It can cause a large variety of symptoms, particularly shortness of breath (SOB) at rest or during exercise, signs of fluid retention such as pulmonary congestion or ankle swelling and objective evidence of an abnormality of the structure or function of the heart at rest. Acute heart failure (AHF) is defined as a rapid onset of signs and symptoms of heart failure resulting in the need for urgent therapy or hospitalization. AHF can present as acute de novo HF (new onset of AHF in a patient without previous cardiac dysfunction) or acute decompensation of chronic HF.

Stroke is defined as an acute focal neurological deficit resulting from a cerebrovascular disease. The two main types of stroke are ischemic and hemorrhagic, accounting for approximately 85% and 15%, respectively. As indicated above, in some specific embodiments the herein disclosed methods for assessing a risk for getting a first cardiovascular event or assessing the risk for cardiovascular mortality are not those, wherein stroke is the first cardiovascular event or wherein the cardiovascular mortality is related to stroke.

Coronary re-vascularization includes percutaneous coronary intervention (PCI) and coronary artery bypass grafting (CABG). Percutaneous coronary intervention (PCI) is a non-surgical procedure used to treat narrowing (stenosis) of the coronary arteries of the heart found in coronary artery disease. After accessing the blood stream through the femoral or radial artery, the procedure uses coronary catheterization to visualize the blood vessels on X-ray imaging. After this, an interventional cardiologist can perform a coronary angioplasty, using a balloon catheter in which a deflated balloon is advanced into the obstructed artery and inflated to relieve the narrowing; certain devices such as stents can be deployed to keep the blood vessel open. Various other procedures can also be performed. Coronary artery bypass surgery, also known as coronary artery bypass graft (CABG, pronounced "cabbage") surgery, and colloquially heart bypass or bypass surgery, is a surgical procedure to restore normal blood flow to an obstructed coronary artery. This surgery is often indicated when coronary arteries have a 50% to 99% obstruction.

Subject matter of the present invention is also the supplementation with selenium in subjects identified to be at high risk of getting a first cardiovascular event or cardiovascular death using the measurement of selenoprotein P and/or fragments thereof, wherein said subject is a current or former smoker.

Subject matter of the present invention is also the supplementation with selenium in subjects identified to be at high risk of getting a first cardiovascular event or cardiovascular death using the measurement of selenoprotein P and/or fragments thereof, wherein stroke is not the first cardiovascular event and wherein the cardiovascular mortality is not related to stroke.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality, wherein stroke is not the first cardiovascular event and wherein the cardiovascular mortality is not related to stroke.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method as described by the present invention.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method as described by the present invention, wherein stroke is not the first cardiovascular event and wherein the cardiovascular mortality is not related to stroke.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method as described by the present invention, wherein the determined level and/or the amount of Selenoprotein P and/or fragments thereof is below a threshold and wherein said threshold is between 4.0 and 5.5 mg/L.

Subject matter of the present invention is selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method as described by the present invention, wherein the determined level and/or the amount of Selenoprotein P and/or fragments thereof is below a threshold and wherein said threshold is between 4.0 and 5.5 mg/L, wherein stroke is not the first cardiovascular event and wherein the cardiovascular mortality is not related to stroke.

Subject matter of the present invention is selenium for use in treatment of a subject having a risk for getting a first cardiovascular event or a risk for cardiovascular mortality wherein said subject has an enhanced risk for getting a first cardiovascular event or a risk for cardiovascular mortality according to any of the before-mentioned embodiments, wherein said subject is a smoker.

Subject matter of the present invention is a kit comprising a box of cigarettes or nicotinic consumables and a tablet comprising selenium.

Subject matter of the present invention is a method of treatment of a subject having a risk for getting a first cardiovascular event or a risk for cardiovascular mortality, wherein selenium is administered to said subject in a pharmaceutically acceptable amount when said subject has an enhanced risk for getting a first cardiovascular event or a risk for cardiovascular mortality.

Subject matter of the present invention is a method of treatment of a subject having a risk for getting a first cardiovascular event or a risk for cardiovascular mortality, wherein selenium is administered to said subject in a pharmaceutically acceptable amount when said subject has an enhanced risk for getting a first cardiovascular event or a risk for cardiovascular mortality, wherein stroke is not the first cardiovascular event and wherein the cardiovascular mortality is not related to stroke.

Subject matter of the present invention is a method of treatment of a subject having a risk for getting a first cardiovascular event or a risk for cardiovascular mortality, wherein selenium is administered to said subject in a pharmaceutically acceptable amount said subject has an enhanced risk for getting a first cardiovascular event or a risk for cardiovascular mortality as determined according to the present invention.

Subject matter of the present invention is a method of treatment of a subject having a risk for getting a first cardiovascular event or a risk for cardiovascular mortality, wherein selenium is administered to said subject in a pharmaceutically acceptable amount said subject has an enhanced risk for getting a first cardiovascular event or a risk for cardiovascular mortality as determined according to the present invention, wherein stroke is not the first cardiovascular event and wherein the cardiovascular mortality is not related to stroke.

Subject matter of the present invention is a method of treatment of a subject having a risk for getting a first cardiovascular event or a risk for cardiovascular mortality according to the above-mentioned embodiment, wherein the determined level and/or the amount of Selenoprotein P and/or fragments thereof is below a threshold and wherein said threshold is between 4.0 and 5.5 mg/L.

Subject matter of the present invention is a method of treatment of a subject having a risk for getting a first cardiovascular event or a risk for cardiovascular mortality according to the above-mentioned embodiment, wherein the determined level and/or the amount of Selenoprotein P and/or fragments thereof is below a threshold and wherein said threshold is between 4.0 and 5.5 mg/L, wherein stroke is not the first cardiovascular event and wherein the cardiovascular mortality is not related to stroke.

Subject matter of the present invention is a method of treatment of a subject having a risk for getting a first cardiovascular event or a risk for cardiovascular mortality according to any of the before-mentioned embodiments wherein said subject is a smoker.

Subject matter of the present invention is a method of treatment of a subject having a risk for getting a first cardiovascular event or a risk for cardiovascular mortality according to any of the before-mentioned embodiments wherein said subject is a smoker, wherein stroke is not the first cardiovascular event and wherein the cardiovascular mortality is not related to stroke.

Subject matter of the present invention is a kit comprising nicotinic consumables and a solid composition comprising selenium. Nicotinic consumables are tobacco-containing consumables, e.g. tobacco-containing cigarettes or cigars or nicotinic patches.

Solid dosage formulations for selenium are, e.g. tablets, capsules, granules, powders, sachets, reconstitutable powders, dry powder inhalers and chewables.

The Kit maybe a kits of parts, meaning that the nicotinic consumables and the solid composition comprising selenium maybe different entities. It is, however, also possible that a solid composition comprising selenium is comprised within the nicotinic consumables, e.g. a powder comprising selenium that is intermixed with the tobacco of the nicotinic consumables.

Subject matter of the present invention is also a method of monitoring a method of treatment according to any of below items 15-23 wherein a method for assessing a risk according to any of below items 1-14 wherein said method is performed at least two times. Thus, selenium is determined in the sample of a subject during the period of administration of the selenium composition to check whether to continue with selenium administration. This determination for monitoring purposes may be conduction at different time points during treatment e.g. once a day, or once a week.

Embodiments of the invention are:
1. A method for assessing a risk for getting a first cardiovascular event or assessing the risk for cardiovascular mortality in a subject, comprising
    a) determining the level and/or the amount of Selenoprotein P and/or fragments thereof in a sample of said subject
    b) correlating the determined level and/or the amount of Selenoprotein P and/or fragments thereof with the risk for getting a first cardiovascular event or assessing the risk for cardiovascular mortality in said subject
2. A method for assessing a risk for getting a first cardiovascular event or assessing the risk for cardiovascular mortality in a subject according to item 1, wherein the risk for getting a first cardiovascular event or assessing the risk for cardiovascular mortality is enhanced when the determined amount level and/or the amount of Selenoprotein P and/or fragments thereof in a sample of said subject is below a threshold.
3. A method for assessing a risk for getting a first cardiovascular event or assessing the risk for cardiovascular mortality in a subject according to item 1, wherein the risk for getting a first cardiovascular event or assessing the risk for cardiovascular mortality is enhanced when said level and/or the amount of Selenoprotein P and/or fragments thereof in said sample is below a threshold wherein said threshold is between 4.0 and 5.5 mg/L.
4. A method for assessing a risk for getting a first cardiovascular event or assessing the risk for cardiovascular mortality in a subject according to items 1-3, wherein the risk for getting a first cardiovascular event or assessing the risk for cardiovascular mortality is enhanced when said level and/or the amount of Selenoprotein P and/or fragments thereof in said sample is below a threshold, wherein said threshold has been determined by the calculation of receiver operating characteristic curves (ROC curves), plotting the value of a variable versus its relative frequency in the "normal" population (e.g. subjects who did not develop the condition) and "disease" population (e.g. subjects who did develop the condition).

5. A method for assessing a risk for getting a first cardiovascular event or assessing the risk for cardiovascular mortality in a subject according to items 1-4, wherein the risk for getting a first cardiovascular event or assessing the risk for cardiovascular mortality is enhanced when said level and/or the amount of Selenoprotein P and/or fragments thereof in said sample is below a threshold, wherein said threshold is the lower normal range of a healthy population e.g. the median 5.5 mg/L, more preferred 5.0 mg/L, even more preferred 4.5 mg/L, most preferred 4.0 mg/L.

6. A method for assessing a risk for getting a first cardiovascular event or assessing the risk for cardiovascular mortality in a subject according to items 1-5, wherein said subject has never had a cardiovascular event and has never had any cardiovascular disease at the time of sample taking.

7. A method for assessing a risk for getting a first cardiovascular event or assessing the risk for cardiovascular mortality in a subject according to items 1-6, wherein said first cardiovascular event is selected from a group comprising myocardial infarction, acute heart failure, stroke, coronary re-vascularization and said cardiovascular mortality is selected from cardiovascular death related to myocardial infarction, stroke or acute heart failure.

8. A method for assessing a risk for getting a first cardiovascular event or assessing the risk for cardiovascular mortality in a subject according to items 1-7, wherein said subject is a current smoker or former smoker.

9. A method for assessing a risk for getting a first cardiovascular event or assessing the risk for cardiovascular mortality in a subject according to items 1-8, wherein said level and/or amount of Selenoprotein P and/or fragments thereof has been determined by an immunoassay using at least one binder, binding to SEQ ID No. 2.

10. A method for assessing a risk for getting a first cardiovascular event or assessing the risk for cardiovascular mortality in a subject according to item 9, wherein said at least one binder is an antibody or a fragment thereof.

11. A method for assessing a risk for getting a first cardiovascular event or assessing the risk for cardiovascular mortality in a subject according to items 1-8, wherein said level and/or amount of Selenoprotein P and/or fragments thereof has been determined by mass spectroscopy.

12. A method for assessing a risk for getting a first cardiovascular event or assessing the risk for cardiovascular mortality in a subject according to items 1-11, wherein said subject does not suffer from diabetes mellitus.

13. A method for assessing a risk for getting a first cardiovascular event or assessing the risk for cardiovascular mortality in a subject according to items 1-12, wherein said risk for getting a first cardiovascular event including death is assessed for a period of time of 10 years, preferred 8 years, preferred 5 years, preferred 2.5 years after taking the sample from said subject.

14. A method for assessing a risk for getting a first cardiovascular event or assessing the risk for cardiovascular mortality in a subject according to items 1-13, wherein the sample is selected from the group comprising whole blood, plasma, and serum.

15. Selenium for use in treatment of a subject having a risk for getting a first cardiovascular event or a risk for cardiovascular mortality, wherein said subject has an enhanced risk for getting a first cardiovascular event or a risk for cardiovascular mortality.

16. Selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method of items 1-14.

17. Selenium for use in treatment of a subject having a risk for getting a first cardiovascular event or a risk for cardiovascular mortality, wherein said subject has an enhanced risk for getting a first cardiovascular event or a risk for cardiovascular mortality as determined according to a method of items 1-14, wherein the determined level and/or the amount of Selenoprotein P and/or fragments thereof is below a threshold and wherein said threshold is between 4.0 and 5.5 mg/L.

18. Selenium for use in treatment of a subject having a risk for getting a first cardiovascular event or a risk for cardiovascular mortality, wherein said subject has an enhanced risk for getting a first cardiovascular event or a risk for cardiovascular mortality according to any of items 15-17, wherein said subject is a current smoker or former smoker.

19. A kit comprising nicotinic consumables and a solid composition comprising selenium.

20. A method of treatment of a subject having a risk for getting a first cardiovascular event or a risk for cardiovascular mortality, wherein selenium is administered to said subject in a pharmaceutically acceptable amount said subject has an enhanced risk for getting a first cardiovascular event or a risk for cardiovascular mortality.

21. A method of treatment of a subject having a risk for getting a first cardiovascular event or a risk for cardiovascular mortality, wherein selenium is administered to said subject in a pharmaceutically acceptable amount said subject has an enhanced risk for getting a first cardiovascular event or a risk for cardiovascular mortality as determined according to a method of items 1-14.

22. A method of treatment of a subject having a risk for getting a first cardiovascular event or a risk for cardiovascular mortality according to item 21, wherein the determined level and/or the amount of Selenoprotein P and/or fragments thereof is below a threshold and wherein said threshold is between 4.0 and 5.5 mg/L.

23. A method of treatment of a subject having a risk for getting a first cardiovascular event or a risk for cardiovascular mortality according to any of items 20-22, wherein said subject is a current smoker or a former smoker.

24. A method of monitoring a method of treatment according to any of items 15-23, wherein a method for assessing a risk according to any of items 1-14 is performed at least two times.

25. A method of treatment of a subject having a risk for getting a first cardiovascular event or a risk for cardiovascular mortality according to any of items 15-24, wherein the selenium administered is selected from the group comprising selenite, selenate or selenomethionine (L-selenomethionine).

26. In specific embodiments of the above items 1 to 25, the first cardiovascular event is not stroke, and/or the cardiovascular mortality is not related to stroke.

EXAMPLES

Example 1: Assay Description

The Selenotest ELISA (Hybsier et al. 2017. *Redox Biology* 11: 403-414; Hybsier et al. 2015. *Perspectives in Science* 3: 23-24), a chromogenic enzyme-linked immunosorbent assay, for the quantitative determination of human selenoprotein P in serum samples was used. The Selenotest ELISA is a sandwich enzyme immunoassay in 96 well plate format and uses two different selenoprotein P specific monoclonal antibodies for the antigen capture and detection steps. The selenoprotein P concentrations of the calibrators and controls were determined by measurements against serial dilutions of NIST SRM 1950 Standard Reference Material. Monoclonal antibodies (Ab) were generated by immunization of mice with an emulsion of purified recombinant Seloprotein P. The specific monoclonal Ab5 was immobilized as capture-Ab, and the specific mAb2, was used as detection-Ab. The lower limit of quantification (LLOQ) was determined at a Selenoprotein P concentration of 11.6 µg/L, and the upper limit of quantification (ULOQ) at 538.4 µg/L, thereby defining the working range at Selenoprotein P concentrations between 11.6 and 538.4 µg/L. The intersection at 20% CV defines the limit of detection (LOD), and was reached at a Selenoprotein P concentration of 6.7 µg/L i.e., around 500-fold below average serum SePP concentrations of well-supplied subjects. The signals were linear on dilution within the working range of the assay, and SePP was stable in serum for 24 h at room temperature. For further details of the assay see Hybsier et al. 2017. *Redox Biology* 11: 403-414.

Example 2: MPP-Study

Study Description

The population-based Malmo Preventive Project (MPP) is a Swedish single-center prospective population-based study. Between 1974 and 1992, a total of 33,346 men and women of the homogenous ethnic background from the Malmo city area were recruited and screened for traditional risk factors of all-cause mortality and cardiovascular disease (CVD). A detailed description of baseline procedures may be found elsewhere (Fedorowski et al. 2010. *Eur Heart J* 31: 85-91; Berglund et al. 1996. *J Intern Med* 239: 489-97). In the years 2002-2006, all survivors from the original MPP cohort were invited for a reexamination. Of these, 18,240 participants (n=6,682 women) responded to the invitation and were reexamined including blood sampling and immediate −80° C. storage of EDTA plasma aliquots. The reexamination in 2002-2006 represents the baseline time point in the current study.

The 5060 of 18240 subjects tested for Selenoprotein P is a random sample (mean age 69 years). 4366 subjects were free from prior CVD (myocardial infarction, stroke and coronary re-vascularizations). Mean follow-up time of patients was 9.3 years, with deaths (n=1111), CVD deaths (n=351) and first CVD event (n=745).

Statistics

Values are expressed as means and standard deviations, medians and interquartile ranges (IQR), or counts and percentages as appropriate. Cox proportional-hazards regression was used to analyze the effect of risk factors on time-to-event endpoints (mortality, CVD death and time to first CVD) in uni- and multivariable analyses. The assumptions of proportional hazard were tested for all variables. SePP concentrations were log-transformed. For all continuous variables, hazard ratios (HR) were standardized to describe the HR for a change of one IQR. Survival curves plotted by the Kaplan-Meier method using SePP quintiles were used for illustrative purposes.

Results

Baseline characteristics of the cohort are shown in table 1.

| Variable | n = 4366 |
| --- | --- |
| Age | 69.4 (6.2) |
| gender male | 3008 (68.9%) |
| Current Smoking | 835 (19.1%) |
| AHT | 1476 (33.8%) |
| HDL | 1.4 (0.4) |
| LDL | 3.7 (1.0) |
| BMI | 27.1 (6.2) |
| SBP | 146.6 (20.3) |
| prevalent Diabetes | 466 (10.7%) |
| Deaths | 1111 (25.4%) |
| CVD Deaths | 351 (8%) |
| first CVD event | 745 (17.1%) |
| SePP (mg/L) | 5.5 [4.5-6.6] |

At baseline subjects in the lowest quintile of SePP have the highest smoking rate (27.5% smokers) versus 16.4 to 18% in quintile 2-5 of SePP (P<0.001).

Low SePP plasma concentration (lowest population quintile=SePP deficiency) strongly and independently predicts cardiovascular mortality and a first cardiovascular event.

Multivariate adjusted analysis (adjusted for age, sex, smoking, BMI, systolic blood pressure, antihypertensive therapy, HDL, LDL, diabetes) revealed that the lowest SePP quintile is strongly and independently associated with cardiovascular mortality (Q1 vs. Q2-5: HR=2.7 (2.3-3.1), p<0.0001; continuous HR (standardized)=0.83 (0.75-0.95), p<0.0001).

Multivariate adjusted analysis (adjusted for age, sex, smoking, BMI, systolic blood pressure, antihypertensive therapy, HDL, LDL, diabetes) revealed that the lowest SePP quintile is strongly and independently associated with a first cardiovascular event (Q1 vs. Q2-5: HR=1.5 (1.4-1.7), p<0.0001; continuous HR (standardized)=0.85 (0.79-0.92), p<0.0001).

FIGURE DESCRIPTION

FIG. 1: FIG. 1 shows Kaplan-Meier Plot for risk of cardiovascular mortality with SePP concentrations.

Figure 2:
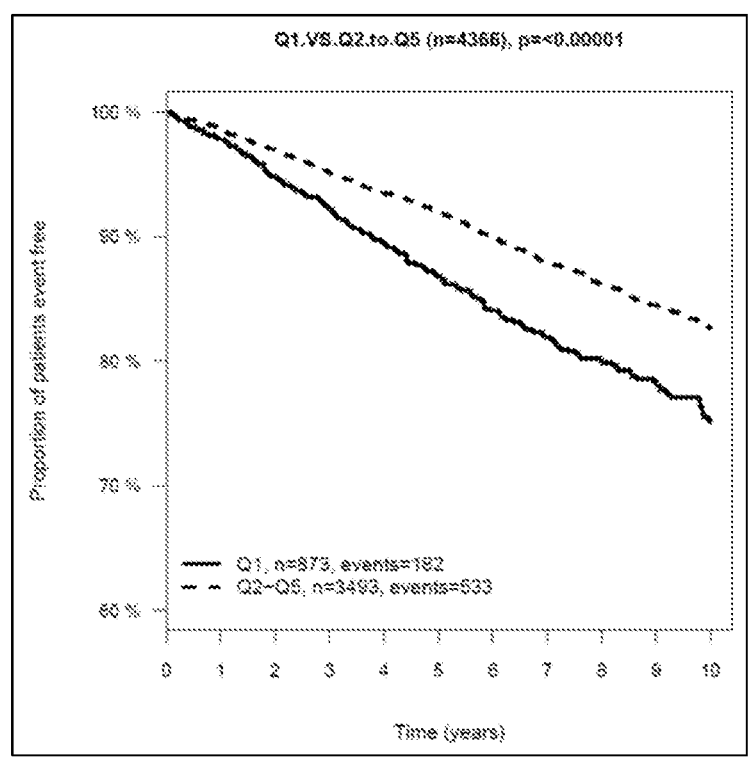

FIG. 2: FIG. 2 shows Kaplan-Meier Plot for risk of first cardiovascular event with SePP concentrations.

```
SEQUENCE LISTING
SEQ ID NO. 1: Selenoprotein P including signal
sequence (amino acid 1 to 381)
MWRSLGLALA LCLLPSGGTE SQDQSSLCKQ PPAWSIRDQD

PMLNSNGSVT VVALLQASUY LCILQASKLE DLRVKLKKEG

YSNISYIVVN HQGISSRLKY THLKNKVSEH IPVYQQEENQ
```

-continued

TDVWTLLNGS KDDFLIYDRC GRLVYHLGLP FSFLTFPYVE

EAIKIAYCEK KCGNCSLTTL KDEDFCKRVS LATVDKTVET

PSPHYHHEHH HNHGHQHLGS SELSENQQPG APNAPTHPAP

PGLHHHHKHK GQHRQGHPEN RDMPASEDLQ DLQKKLCRKR

CINQLLCKLP TDSELAPRSU CCHCRHLIFE KTGSAITUQC

KENLPSLCSU QGLRAEENIT ESCQURLPPA AUQISQQLIP

TEASASURUK NQAKKUEUPS N

SEQ ID NO. 2: secreted Selenoprotein P
(amino acid 20 to 381)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

UCCHCRHLIF EKTGSAITUQ CKENLPSLCS UQGLRAEENI

TESCQURLPP AAUQISQQLI PTEASASURU KNQAKKUEUP

SN

SEQ ID NO. 3: Selenoprotein P (amino acid
200 to 346)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

UCCHCRHLIF EKTGSAITUQ CKENLPSLCS UQGLRAEENI

TESCQUR

SEQ NO. 4: Selenoprotein P (amino acid
20 to 298)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPR

SEQ ID NO. 5: Selenoprotein P (amino acid
20 to 299)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

SEQ ID NO. 6: Selenoprotein P (amino acid
20 to 300)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS U

SEQ ID NO. 7: Selenoprotein P (amino acid
20 to 301)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

UC

SEQ ID NO. 8: Selenoprotein P (amino acid
20 to 302)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

UCC

SEQ ID NO. 9: Selenoprotein P (amino acid
20 to 303)
ESQDQSSLCK QPPAWSIRDQ DPMLNSNGSV TVVALLQASU

YLCILQASKL EDLRVKLKKE GYSNISYIVV NHQGISSRLK

YTHLKNKVSE HIPVYQQEEN QTDVWTLLNG SKDDFLIYDR

CGRLVYHLGL PFSFLTFPYV EEAIKIAYCE KKCGNCSLTT

LKDEDFCKRV SLATVDKTVE TPSPHYHHEH HHNHGHQHLG

SSELSENQQP GAPNAPTHPA PPGLHHHHKH KGQHRQGHPE

NRDMPASEDL QDLQKKLCRK RCINQLLCKL PTDSELAPRS

UCCH

SEQ ID NO. 10: Selenoprotein P (amino acid 20 to 304)
ESQDQSSLCK QPPAWSIRDQ DPMLNSNGSV TVVALLQASU
YLCILQASKL EDLRVKLKKE GYSNISYIVV NHQGISSRLK
YTHLKNKVSE HIPVYQQEEN QTDVWTLLNG SKDDFLIYDR
CGRLVYHLGL PFSFLTFPYV EEAIKIAYCE KKCGNCSLTT
LKDEDFCKRV SLATVDKTVE TPSPHYHHEH HHNHGHQHLG
SSELSENQQP GAPNAPTHPA PPGLHHHHKH KGQHRQGHPE
NRDMPASEDL QDLQKKLCRK RCINQLLCKL PTDSELAPRS
UCCHC SEQ ID NO. 11: Selenoprotein P (amino acid 20 to 305)
ESQDQSSLCK QPPAWSIRDQ DPMLNSNGSV TVVALLQASU
YLCILQASKL EDLRVKLKKE GYSNISYIVV NHQGISSRLK
YTHLKNKVSE HIPVYQQEEN QTDVWTLLNG SKDDFLIYDR
CGRLVYHLGL PFSFLTFPYV EEAIKIAYCE KKCGNCSLTT
LKDEDFCKRV SLATVDKTVE TPSPHYHHEH HHNHGHQHLG
SSELSENQQP GAPNAPTHPA PPGLHHHHKH KGQHRQGHPE
NRDMPASEDL QDLQKKLCRK RCINQLLCKL PTDSELAPRS
UCCHCR SEQ ID NO. 12: Selenoprotein P (amino acid 20 to 306)
ESQDQSSLCK QPPAWSIRDQ DPMLNSNGSV TVVALLQASU
YLCILQASKL EDLRVKLKKE GYSNISYIVV NHQGISSRLK
YTHLKNKVSE HIPVYQQEEN QTDVWTLLNG SKDDFLIYDR
CGRLVYHLGL PFSFLTFPYV EEAIKIAYCE KKCGNCSLTT
LKDEDFCKRV SLATVDKTVE TPSPHYHHEH HHNHGHQHLG
SSELSENQQP GAPNAPTHPA PPGLHHHHKH KGQHRQGHPE
NRDMPASEDL QDLQKKLCRK RCINQLLCKL PTDSELAPRS
UCCHCRH SEQ ID NO. 13: Selenoprotein P (amino acid 1 to 235)
MWRSLGLALA LCLLPSGGTE SQDQSSLCKQ PPAWSIRDQD
PMLNSNGSVT VVALLQASUY LCILQASKLE DLRVKLKKEG
YSNISYIVVN HQGISSRLKY THLKNKVSEH IPVYQQEENQ
TDVWTLLNGS KDDFLIYDRC GRLVYHLGLP FSFLTFPYVE
EAIKIAYCEK KCGNCSLTTL KDEDFCKRVS LATVDKTVET
PSPHYHHEHH HNHGHQHLGS SELSENQQPG APNAP SEQ ID NO. 14: Selenoprotein P (amino acid 279 to 381)
KRCINQLLCK LPTDSELAPR SUCCHCRHLI FEKTGSAITU
QCKENLPSLC SUQGLRAEEN ITESCQURLP PAAUQISQQL
IPTEASASUR UKNQAKKUEU PSN SEQ ID NO. 15: Selenoprotein P (amino acid 312 to 381)
TGSAITUQCK ENLPSLCSUQ GLRAEENITE SCQURLPPAA
UQISQQLIPT EASASURUKN QAKKUEUPSN

---

The invention claimed is:

1. A method comprising:
measuring an amount of Selenoprotein P and/or fragments thereof in a sample comprising bodily fluid from a subject and a binder to Selenoprotein P and/or fragments thereof,
and selecting a subject, in need of treatment to reduce the likelihood of a cardiovascular event selected from myocardial infarction, acute heart failure, stroke, coronary re-vascularization, atherosclerosis, or cardiovascular mortality, who has an amount of Selenoprotein P and/or fragments thereof bound to said binder in said sample that is less than the median of a distribution of the level of Selenoprotein P and/or fragments thereof bound to said binder in a population of subjects who did not develop said cardiovascular event or cardiovascular mortality, and wherein said subject in need thereof has not experienced any of said cardiovascular event.

2. The method of claim 1, wherein said cardiovascular event is selected from a group consisting of myocardial infarction, acute heart failure, stroke, and coronary revascularization, and said cardiovascular mortality is related to cardiovascular death caused by myocardial infarction, stroke or acute heart failure.

3. The method of claim 1, wherein said subject is a current smoker or former smoker.

4. The method of claim 1, wherein said Selenoprotein P and/or fragments thereof is bound to said binder via SEQ ID No. 2.

5. The method of claim 1, wherein said amount of Selenoprotein P and/or fragments thereof bound to said binder has been determined by mass spectroscopy.

6. The method of claim 1, wherein said subject does not suffer from diabetes mellitus.

7. The method of claim 1, wherein the bodily fluid is selected from the group consisting of whole blood, plasma, and serum.

8. A method of treatment to reduce the likelihood of a cardiovascular event selected from myocardial infarction, acute heart failure, stroke, coronary re-vascularization, atherosclerosis, or cardiovascular mortality comprising:
   administering a pharmaceutically acceptable amount of selenium to a subject in need thereof selected in claim 1.

9. The method of claim 8, wherein said subject is a current smoker or a former smoker.

10. The method of claim 8, wherein the selenium administered is selected from the group consisting of selenite, selenate and selenomethionine (L-selenomethionine).

* * * * *